US011293926B2

(12) United States Patent
Toyoda

(10) Patent No.: US 11,293,926 B2
(45) Date of Patent: Apr. 5, 2022

(54) METHOD FOR PREPARING SUGAR CHAIN

(71) Applicant: SUMITOMO BAKELITE CO., LTD., Tokyo (JP)

(72) Inventor: Masaaki Toyoda, Tokyo (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 262 days.

(21) Appl. No.: 16/084,454

(22) PCT Filed: Feb. 28, 2018

(86) PCT No.: PCT/JP2018/007493
§ 371 (c)(1),
(2) Date: Sep. 12, 2018

(87) PCT Pub. No.: WO2018/186063
PCT Pub. Date: Oct. 11, 2018

(65) Prior Publication Data
US 2019/0369105 A1    Dec. 5, 2019

(30) Foreign Application Priority Data

Apr. 4, 2017  (JP) .............................. JP2017-074655

(51) Int. Cl.
*G01N 33/58*    (2006.01)
*C12Q 1/34*    (2006.01)
*C12P 19/04*    (2006.01)

(52) U.S. Cl.
CPC ............. *G01N 33/582* (2013.01); *C12Q 1/34* (2013.01); *C12P 19/04* (2013.01)

(58) Field of Classification Search
CPC ...... G01N 33/582; G01N 33/58; G01N 33/48; C12Q 1/34
See application file for complete search history.

(56) References Cited

U.S. PATENT DOCUMENTS

| 5,569,366 | A  | 10/1996 | Chen et al. |
| 8,828,732 | B2 | 9/2014  | Abe et al. |
| 2004/0259150 | A1 | 12/2004 | Nakamura et al. |
| 2011/0046364 | A1 | 2/2011  | Abe et al. |

FOREIGN PATENT DOCUMENTS

| EP | 00867722 A2 | 9/1998 |
| JP | 2003160596 A | 6/2003 |
| JP | 2013-70682 A | 4/2013 |
| WO | 2003/085119 A1 | 10/2003 |
| WO | 2009/133696 A1 | 11/2009 |

OTHER PUBLICATIONS

Glycan mass, 2016, pp. 1-2, downloaded on Feb. 13, 2020 from http://www.ionsource.com/Card/carbo/carbstr.htm (Year: 2016).*
Tayi et al., J. Biol. Methods, 2015, 2(2):e19, pp. 1-9. (Year: 2015).*
Bigge et al., "Nonselective and Efficient Fluorescent Labeling of Glycans Using 2-Amino Benzamide and Anthranilic Acid", Analytical Biochemistry, 1995, 230, pp. 229-238, cited in Specification (11 pages).
"Product Guide for LudgerTag™ 2-AB(2-aminobenzamide) Glycan Labeling Kit containing 2-picoline borane", Ludger Document # LT-KAB-VP24-Guide-v2.0, Ludger Limited, 2013, pp. 1-32, cited in Specification, Japanese Notification of Reasons for Refusal and Japanese Decision to Grant a Patent (32 pages).
"Product Guide for LudgerTag™ 2-AB(2-aminobenzamide) Glycan High Throughput Labeling Kit containing 2-picoline borane",Ludger Document# LT-KAB-VP96-Guide-v1.0, Ludger Limited, 2015, pp. 1-6, cited in ISR (6 pages).
Sato et al., "One-pot reductive amination of aldehydes and ketones with α-picoline-borane in methanol, in water, and in neat conditions", Science Direct, Tetrahedron, 60, 2004, pp. 7899-7906 (8 pages).
Decision to Grant a Patent dated Oct. 3, 2017, Issued in counterpart Japanese Patent Application No. 2017-074655, w/English translation (6 pages).
Notification of Reasons for Refusal dated May 9, 2017, Issued in counterpart Japanese Patent Application No. 2017-074655, w/English translation (4 pages).
International Search Report in Japanese and Written Opinion in Japanese dated May 22, 2018, issued in counterpart International Application No. PCT/JP2018/007493 (6 pages).
Extended European Search Report dated Nov. 14, 2019, issued in European Patent Application No. 18780997.5 (PCT/JP2018007493).
Office Action dated Mar. 25, 2019, issued in counterpart KR Application No. 10-2018-7028249, with English translation (9 pages).

* cited by examiner

*Primary Examiner* — Allison M Fox
*Assistant Examiner* — Qing Xu
(74) *Attorney, Agent, or Firm* — WHDA, LLP

(57) ABSTRACT

Provided is a method for preparing a sugar chain, including: a labeling step of adding a labeling reagent to a sugar chain-containing sample which contains a sugar chain to obtain a labeled product containing a labeled substance of the sugar chain, in which a reaction environment of the labeling reagent and the sugar chain contains water in the labeling step.

12 Claims, 4 Drawing Sheets

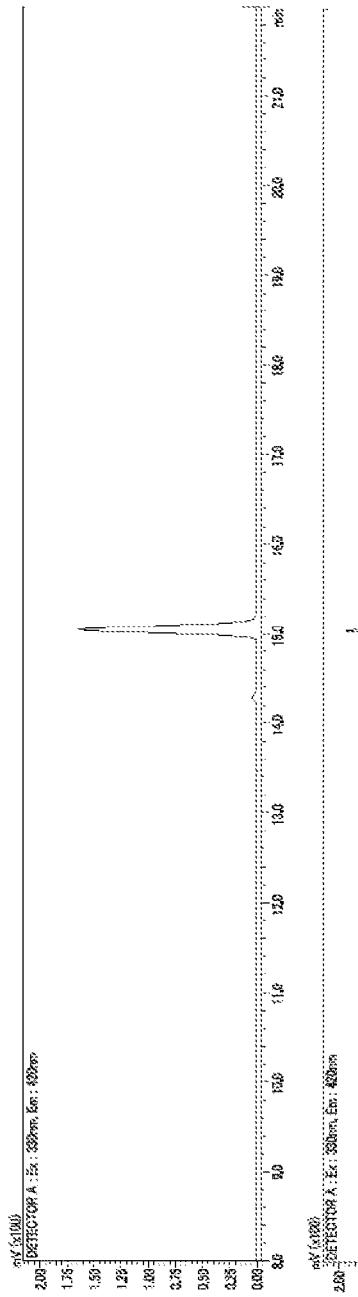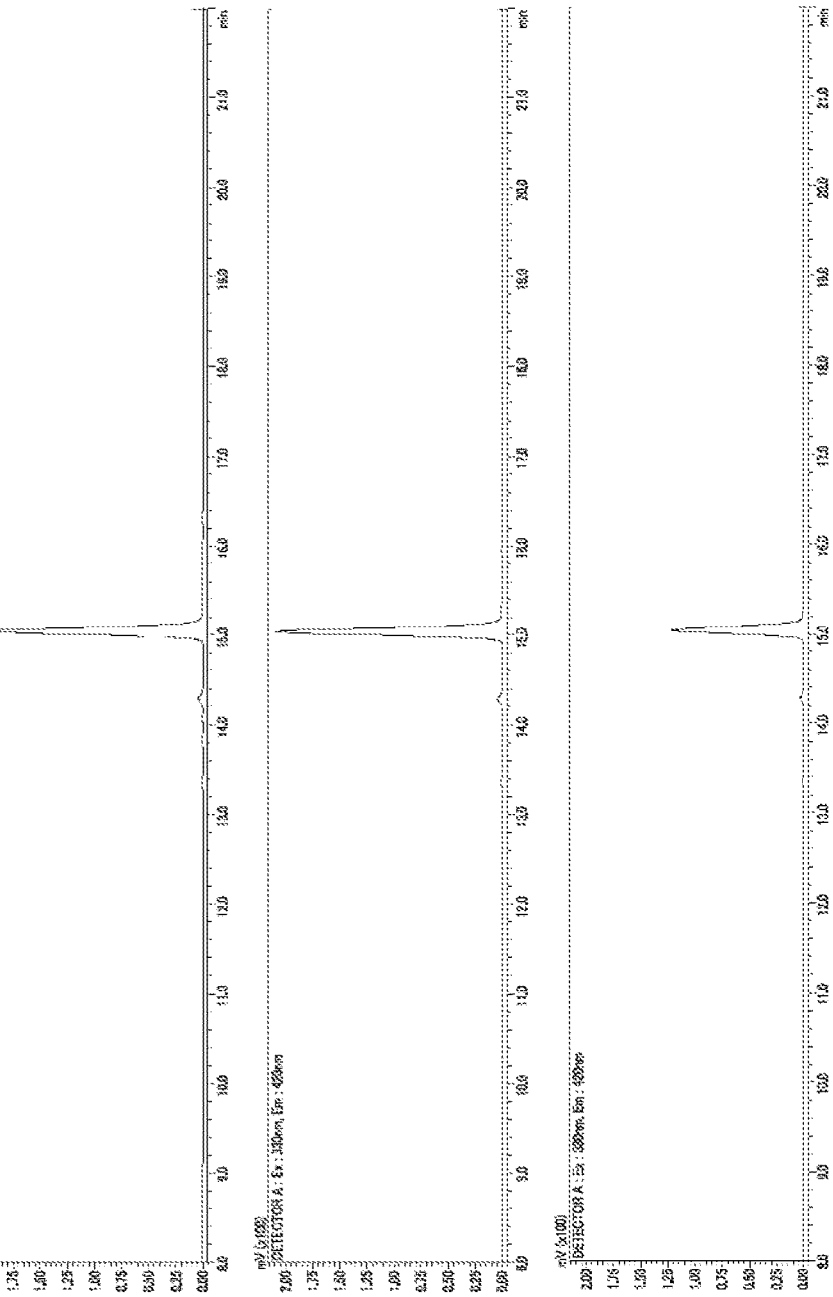
FIG. 1 (a)
FIG. 1 (b)
FIG. 1 (c)
FIG. 1 (d)

METHOD FOR PREPARING SUGAR CHAIN

TECHNICAL FIELD

The present invention relates to a method for preparing a sugar chain.

BACKGROUND ART

In regard to a method for preparing a sugar chain, various developments on a sugar chain labeling technology have been made. As this kind of technology, those described in Patent Document 1 have been known. Patent Document 1 describes that a sugar chain captured by beads in a completely dried and hardened state is labeled using a typical labeling reagent such as 2-aminobenzamide or 2-aminopyridine (paragraphs 0056 to 0061 in Patent Document 1).

Patent Document 1 describes that a 30% acetic acid/DMSO mixed solvent is used as a labeling reagent so that the final concentrations of 2-aminobenzamide (2-AB) and sodium cyanoborohydride are respectively set to 0.35 M and 1 M (paragraph 0059 of Patent Document 1). Similarly, Non-Patent Document 1 describes the composition of a labeling reagent obtained by using 2-AB.

Further, Non-Patent Document 2 is a guide that describes procedures for using a glycan labeling kit obtained by using 2-AB.

RELATED DOCUMENT

Patent Document

[Patent Document 1] WO2009/133696A

[Non-Patent Document 1] J. C Bigge, T. P Patel, J. A Bruce, P. N Goulding, S. M Charles, R. B Parekh. "Nonselective and Efficient Fluorescent Labeling of Glycans Using 2-Amino Benzamide and Anthranilic Acid" Analytical Biochemistry 1995 Sep. 20 230(2): p. 229 to 238

[Non-Patent Document 2] Product Guide for LudgerTag™2-AB(2-aminobenzamide) Glycan Labeling Kit containing 2-picoline 15 borane, Ludger Document # LT-KAB-VP24-Guide-v2.0, published by Ludger Limited, created on Dec. 11, 2013 (updated on Sep. 26, 2016), p. 1-32

SUMMARY OF THE INVENTION

Technical Problem

In the technical field of sugar chain labeling, sugar chain labeling has been known to perform in a dry environment in which moisture is completely evaporated as a typical protocol, as described in Patent Document 1 or the like. Further, a solvent which does not contain added water has been typically used as a mixed solvent of a labeling reagent such as 2-AB.

However, as the result of examination conducted by the present inventors, it was found that there is room for further improvement in terms of labeling efficiency in the sugar chain labeling method described in Patent Document 1.

Solution to Problem

After the examination of the present inventors, it was found that the labeling efficiency can be improved by appropriately controlling the reaction environment of a sugar chain and a labeling reagent.

As the result of further intensive research based on these findings, it was found that the labeling efficiency of a sugar chain can be further improved than the labeling efficiency of Patent Document 1 by allowing the reaction environment of the sugar chain and the labeling reagent to contain water, which is different from the known typical sugar chain labeling protocol (sugar chain labeling is performed in a dry environment in which moisture is completely evaporated).

The detailed mechanism is not clear, but it is considered that the dispersibility of a labeling reagent such as 2-AB in a mixed solvent is increased because of the high polarity of water and thus the labeling efficiency of the sugar chain is improved.

In addition, as the result of further examination, it was found that, using "X/Y" representing the ratio of a moisture amount Y to a sugar chain amount X as an index, the sugar chain labeling can be efficiently performed by appropriately controlling the lower limit of X/Y and the concentration of a labeling reagent in a reaction environment system is decreased due to an excessive amount of water by controlling the upper limit of X/Y, and accordingly, the labeling efficiency is decreased. Therefore, the present invention has been completed.

According to the present invention, there is provided a method for preparing a sugar chain, including: a labeling step of adding a labeling reagent to a sugar chain-containing sample which contains a sugar chain to obtain a labeled product containing a labeled substance of the sugar chain, in which a reaction environment of the labeling reagent and the sugar chain contains water in the labeling step, and in a case where an amount of the water in the reaction environment is set as X (μL) and an amount of the sugar chain is set as Y (μg) in the labeling step, X/Y is greater than or equal to 1.2 and less than or equal to 50.

Further, as the result of further intensive examination on the reaction environment of a sugar chain and a labeling reagent, the detailed mechanism of a sugar chain that is present in the reaction environment at a low concentration is not clear, but the present inventors found a new finding on a small scale in that the labeling efficiency can be improved even with a trace amount of water. Therefore, the present invention has been completed.

According to the present invention, there is provided a method for preparing a sugar chain, including: a labeling step of adding a labeling reagent to a sugar chain-containing sample which contains a sugar chain to obtain a labeled product containing a labeled substance of the sugar chain, in which a reaction environment of the labeling reagent and the sugar chain contains water in the labeling step, and in a case where an amount of the sugar chain is greater than 0 μg and less than 1 μg in the labeling step, an amount of water in the reaction environment is greater than 0 μL and less than or equal to 1.0 μL.

Advantageous Effects of Invention

According to the present invention, a method for preparing a sugar chain with excellent labeling efficiency is provided.

BRIEF DESCRIPTION OF THE DRAWINGS

The foregoing and other objects, the features, and the advantages will become apparent from the preferred embodiments described below and the accompanying drawings.

FIGS. 1(a) to 1(d) show HPLC spectra obtained in Examples 1 to 3 and Comparative Example 1.

DESCRIPTION OF EMBODIMENTS

Figure 2:
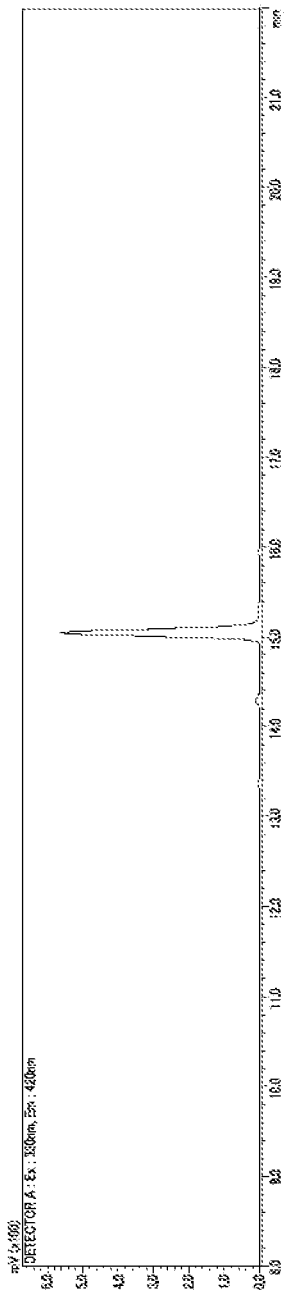
FIGS. 2(a) to 2(c) show HPLC spectra obtained in Examples 4 and 5 and Comparative Example 2.
Figure 2:
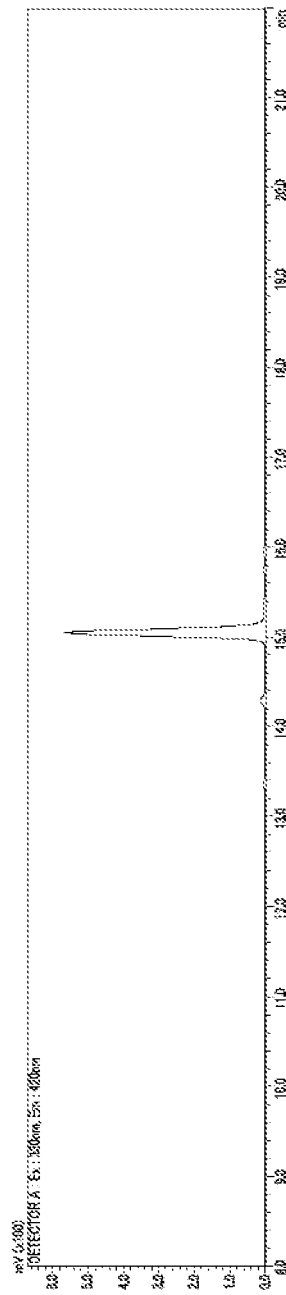
Figure 2:
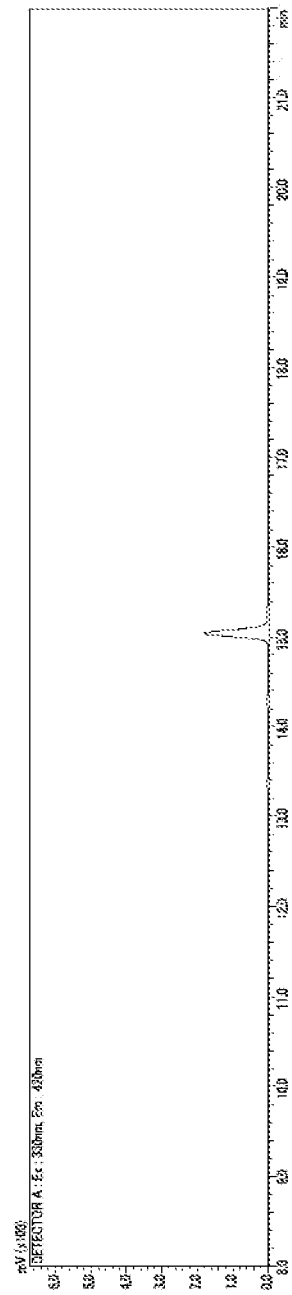

Hereinafter, embodiments of the present invention will be described with reference to the accompanying drawings. Further, in all drawings, the same constituent elements are denoted by the same reference numerals, and the description thereof will not be repeated.

An outline of a method for preparing a sugar chain of the present embodiment will be described.

The method for preparing a sugar chain of the present embodiment includes a labeling step of adding a labeling reagent to a sugar chain-containing sample which contains a sugar chain to obtain a labeled product containing a labeled substance of the sugar chain, in which a reaction environment of the labeling reagent and the sugar chain contains water in the labeling step.

According to the method for preparing a sugar chain of the present embodiment, the labeling efficiency of a sugar chain can be further improved than the labeling efficiency of Patent Document 1 by allowing the reaction environment of the sugar chain and the labeling reagent to contain water. The detailed mechanism is not clear, but it is considered that the dispersibility of a labeling reagent such as 2-AB in a mixed solvent is increased because of the high polarity of water and thus the labeling efficiency of the sugar chain is improved.

Therefore, according to the method for preparing a sugar chain of the present embodiment, a sugar chain labeling protocol with excellent sugar chain labeling efficiency can be realized.

Hereinafter, each step of the method for preparing a sugar chain of the present embodiment will be described in detail.

According to an example of the method for preparing a sugar chain of the present embodiment, the method may include a labeling step of adding a labeling reagent to a sugar chain-containing sample which contains a sugar chain to obtain a labeled product containing a labeled substance of the sugar chain.

(Glycoprotein)

In the present embodiment, a sugar chain derived from a glycoprotein can be used as the sugar chain.

The glycoprotein may be a protein containing at least a sugar chain as a composite component. A glycoprotein sugar chain portion may be of an N-binding type or an O-binding type. Further, a sugar chain portion may have a natural structure or may be artificially modified. In addition, the sugar chain portion may be formed of a neutral sugar chain or an acidic sugar chain. A sugar chain binding site in a glycoprotein may be a site which is the same as a natural product or may be a site to which a sugar chain is not bonded in a natural product.

The sugar chain contains monosaccharides or polysaccharides. There may be used alone or in combination of two or more kinds thereof.

A protein portion of a glycoprotein may be folded so as to incorporate the sugar chain portion therein in a state before denaturation. The molecular weight of such a protein portion may be, for example, greater than or equal to 1 kDa or greater than or equal to 10 kDa. The upper limit of the molecular weight of the protein portion is not particularly limited and may be, for example, 1000 kDa.

Specific examples of the glycoprotein include physiologically active substances selected from the group consisting of an antibody, a hormone, an enzyme, and a complex containing these. Here, examples of the complex include a complex of an antigen and an antibody, a complex of a hormone and a receptor, and a complex of an enzyme and a substrate. These glycoproteins can be used as physiologically active substances prepared by cell culture engineering.

Further, a glycoprotein may contain an antibody. Examples of the antibody include an immunoglobulin such as IgG, IgM, IgA, IgD, or IgE; a low-molecular-weight antibody such as Fab, F(ab'), F(ab')$_2$, a single-chain antibody (scFv), or a bispecific antibody (diabody); an Fc-containing molecule such as an Fc fusion protein or a peptide configured by fusion between an Fc region and another functional protein or a peptide; and a chemically modified antibody obtained by adding a chemically modifying group such as a radioactive isotope coordinating chelate or polyethylene glycol. Further, the antibody may be a monoclonal antibody or a polyclonal antibody.

Further, the antibody may be an antibody pharmaceutical candidate or an antibody pharmaceutical product. The antibody pharmaceutical candidate is a substance obtained in the process of developing an antibody pharmaceutical product and used for evaluating the activity and the safety as an antibody pharmaceutical product.

<Isolation Step>

According to an example of the method for preparing a sugar chain of the present embodiment, the method may include an isolation step of acting a sugar chain-isolating enzyme on a sample in a state of being fixed to a solid phase to obtain the sugar chain-containing sample which contains the sugar chain, before the labeling step. In this manner, the sugar chain can be rapidly cut out.

(Sample)

In the present embodiment, the sample fixed to a solid phase may contain the glycoprotein.

The sample containing a glycoprotein fixed to a solid phase can be obtained by bringing a sample containing a glycoprotein into contact with the solid phase to capture the glycoprotein. In the sample containing a glycoprotein to be brought into contact with the solid phase, the glycoprotein may not be purified (separation of the glycoprotein from the impurities) from the viewpoint of rapidly performing preparation of a sugar chain. Examples of the sample include body fluid such as blood (for example, serum or plasma), lymph fluid, peritoneal exudate fluid, interstitial fluid, cerebrospinal fluid, or ascites fluid; a culture supernatant of antibody producing cells such as B cells, hybridomas, or CHO cells; and ascites fluid of animals to which antibody producing cells are transplanted. The sample may be a mixture of glycoprotein variations in which the protein portion is uniform and the sugar chain portion is non-uniform, such as a glycoprotein preparation obtained by cell culture engineering of a culture supernatant or the like.

The sample containing a protein fixed to the solid phase may be a product obtained by solid phase synthesis of a glycoprotein in addition to those described above.

The concentration of the glycoprotein in the sample containing a glycoprotein to be brought into contact with the solid phase is not particularly limited, but may be in a range of 0.1 μg/mL to 50 mg/mL. It is preferable that the concentration thereof is greater than or equal to the above-described lower limit from the viewpoint of detectability. It is preferable that the concentration thereof is less than or equal to the above-described upper limit from the viewpoint of quantitativity.

The glycoprotein to be brought into contact with the solid phase may be in a range of 0.001 μg to 100 mg or in a range of 0.001 μg to 5 mg per one container. It is preferable that the amount of glycoprotein is greater than or equal to the above-described lower limit from the viewpoint of the detection. Since the number of steps is small and the sample loss is extremely small in the method of the present embodiment, the method is particularly useful in a case where the glycoprotein has a small scale (particularly in a range of 0.001 to 500 μg). It is preferable that the amount of glycoprotein is less than or equal to the above-described upper limit from the viewpoint of quantitativity.

The sample containing the glycoprotein fixed to the solid phase may be prepared in a state in which the glycoprotein fixed to the solid phase is dispersed in a liquid component or in a state in which the liquid component is separated.

Further, the sample containing the glycoprotein fixed to the solid phase may contain impurities at the time when the capturing of the glycoprotein by bringing the sample containing the glycoprotein into contact with the solid phase is completed or when the solid phase synthesis is completed. Examples of the impurities include components contained in the sample containing the glycoprotein to be fixed to the solid phase; and a reagent used for the solid phase synthesis of the glycoprotein. More specifically, examples of the impurities include salts, low-molecular-weight compounds, proteins (proteins which are not bonded to the solid phase), and other biological molecules.

Accordingly, as the sample containing the glycoprotein fixed to the solid phase, a sample on which a cleaning treatment is performed after the capturing of the glycoprotein is completed or the solid phase synthesis is completed. In this manner, impurities can be removed while the glycoprotein is fixed to the solid phase. The cleaning can be performed by allowing the cleaning solution to permeate into the solid phase. Examples of the liquid permeation include methods of natural fall, suction, pressurization, and centrifugation.

As the cleaning solution, a solution having a composition and a liquid property, in which a bond between the protein portion of the glycoprotein and the linker in the surface of the solid phase is not cut, is appropriately selected by those skilled in the art. Specifically, a buffer solution, other aqueous solutions, and water may be used. In a case of using an aqueous solution, the pH thereof is preferably in a range of 5 to 10. In a case where the pH of the aqueous solution is in the above-described range, the activity of a sugar chain-isolating enzyme that is used in the subsequent step is easily maintained. Further, in a case where the glycoprotein is fixed to the solid phase by a non-covalent bond, the isolation of the glycoprotein is easily prevented. In a case of using a buffer solution, examples of the buffer include ammonium salts such as ammonium carbonate, ammonium bicarbonate, ammonium chloride, diammonium hydrogen citrate, and ammonium carbamate; a tris buffer such as trishydroxymethylammonium; and a phosphate.

(Solid Phase)

According to the method of the present embodiment, as the form of fixation of glycoprotein in the sample to a solid phase, a non-covalent bond (a hydrogen bond or an ionic bond) due to a specific bond and a covalent bond are exemplified. In addition, the examples do not include the form in which a glycoprotein is merely held by being applied to an electrophoretic gel or being transferred to a blotting membrane. In a case where the glycoprotein is fixed by a non-covalent bond, it is preferable that a binding rate constant ka (unit: $M^{-1}s^{-1}$) has an affinity of, for example, greater than or equal to $10^3$, greater than or equal to $10^4$, $10^3$ to $10^5$, or $10^4$ to $10^5$.

The solid phase to which a glycoprotein is fixed is not particularly limited as long as the solid phase is a carrier having a linker, which is non-covalently or covalently linked to a protein portion of a glycoprotein, on the surface thereof.

Examples of the linker included in the surface of the carrier include a ligand capable of capturing a protein portion of a glycoprotein. Examples of the ligand include a molecule (hereinafter, also simply referred to as a molecule having an affinity for a glycoprotein) having an affinity for a protein portion of a glycoprotein and a carrier in which an ion exchange group or a hydrophobic group is chemically modified in the surface.

The molecule having an affinity for a glycoprotein is not particularly limited and can be easily determined by those skilled in the art according to the glycoprotein to be captured. Examples thereof include a peptidic or proteinous ligand, an aptamer (synthetic DNA, synthetic RNA, or a peptide which can be specifically bonded to a glycoprotein), and a chemically synthetic ligand (a thiazole derivative or the like).

For example, in a case where the glycoprotein is an antibody, the molecule having an affinity for a glycoprotein may be specifically bonded to an antibody or an Fc-containing molecule which is a constant region of an antibody. More specifically, examples of the peptidic or proteinous ligand include a microorganism-derived ligand such as protein A, protein G, protein L, protein H, protein D, or protein Arp; a functional variant (analog substance) obtained by recombinant expression of these ligands; and recombinant protein such as an antibody Fc receptor. In this manner, it is possible to prepare and analyze a sugar chain sample having excellent throughput properties with respect to an antibody with a particularly high importance for sugar chain analysis.

The ion exchange group is not particularly limited as long as the ion exchange group is a functional group which is capable of capturing a glycoprotein using an ion exchange function and capable of releasing a glycoprotein by a counter ion in an ionic strength dependent manner. Preferred examples thereof include cation exchange groups such as a carboxyl group (more specifically, a carboxymethyl group or the like) and a sulfonic acid group (more specifically, a sulfoethyl group, a sulfopropyl group, or the like) As the ion exchange group, anion exchange groups such as a quaternary amino group may be used.

Examples of the hydrophobic group include an alkyl group having 2 to 8 carbon atoms and an aryl group having 2 to 8 carbon atoms. More specifically, examples thereof include a butyl group, a phenyl group, and an octyl group. These groups may be used alone or in combination of two or more kinds thereof.

In addition to those described above, the linker included in the surface of a carrier may be a linking group which is covalently bonded to a C terminal of a C terminal amino acid residue serving as a constituent element of a protein portion of a glycoprotein. Examples of such a linking group include a linking group derived from an amino group-containing compound serving as a solid phase surface modification reagent used for peptide-solid phase synthesis.

The carrier is not particularly limited as long as the carrier is a base material which is insoluble in water and is capable of fixing the above-described linker, and examples thereof include an organic carrier, an inorganic carrier, and a composite carrier. Examples of the organic carrier include synthetic polymers such as cross-linked polyvinyl alcohol, cross-linked polyacrylate, cross-linked polyacrylamide, and cross-linked polystyrene; and carriers formed of polysaccharides such as cross-linked sepharose, crystalline cellulose, cross-linked cellulose, cross-linked amylose, cross-linked agarose, and cross-linked dextran. These may be used alone or in combination of two or more kinds thereof. Examples of the inorganic carrier include glass beads, silica gel, and monolith silica.

An inorganic carrier is unlikely to contain water while an organic carrier has a property of easily containing water. According to the method of the present embodiment, since various reactions are carried out on a solid phase, it is preferable to use an inorganic carrier which is unlikely to contain water. In this manner, effects of an enzyme and/or a reagent are not reduced, which is preferable. The prevention of reduction in effects of an enzyme and/or a reagent contributes to prevention of detection for unnecessary signals during analysis. Therefore, it is preferable to use an inorganic carrier as a carrier. Further, when the carriers are inorganic carriers, for example, some carriers are not isolated by a sugar chain-isolating enzyme and elution of sugar remaining in a resin does not occur from the beginning in a case where a sugar-derived resin is used. Accordingly, appearance of unnecessary signals is easily suppressed during analysis of an isolated sugar chain.

The shape of the carrier is not particularly limited, but may be particulate or non-particulate. In a case of a particulate carrier (bead), a porous carrier may be used. In the case of a particulate carrier, the average particle diameter may be in a range of 1 to 100 µm. It is preferable that the average particle diameter is greater than or equal to the above-described lower limit from the viewpoint of liquid permeability. It is preferable that the average particle diameter is less than or equal to the above-described upper limit from the viewpoint of preventing a decrease in theoretical plate number.

Examples of the non-particulate carrier include monolith type silica gel and a membrane body. The monolith type silica gel is a bulk body of silica gel having micrometer-sized three-dimensional net-like pores (macropores) and nanometer-sized pores (mesopores). The diameter of the macropores may be in a range of 1 to 100 µm, in a range of 1 to 50 µm, in a range of 1 to 30 µm, or in a range of 1 to 20 µm. It is preferable that the diameter of the macropore is greater than or equal to the above-described lower limit from the viewpoint of liquid permeability. It is preferable that the diameter of the macropore is less than or equal to the above-described upper limit from the viewpoint of preventing a decrease in theoretical plate number. The diameter of the mesopore may be in a range of 1 to 100 nm or in a range of 1 to 50 nm. In this manner, it is possible to efficiently capture sugar.

The use volume (the volume of the carrier includes the volume of voids at the time of filling in a case of the particulate carrier and the volume of the carrier includes the volume of mesopores and macropores in a case of the non-particulate carrier) of the carrier may be in a range of 0.001 to 0.1 cm$^3$ or in a range of 0.001 to 0.01 cm$^3$. It is preferable that the volume is greater than or equal to the above-described lower limit from the viewpoint of preventing a decrease in theoretical plate number. It is preferable that the volume is less than or equal to the above-described upper limit from the viewpoint of liquid permeability. Further, when the volume is in the above-described range, a separate liquid after elution can be easily obtained at a concentration suitable for HPLC analysis.

In the present embodiment, the solid phase may have a column structure, a cartridge structure, or the like. Such a solid phase is formed to have a predetermined filter shape with a non-particulate carrier. For example, the solid phase may be formed to be integrated with a portion of a container or detachably fixed into a container as an individual member.

The solid phase may be used in a state of filling a container such as each well of a column and a multi-well plate; each well of a filter plate; or a micro-tube.

The isolation step according to the present embodiment may be performed in a container. In other words, the sample containing the glycoprotein fixed to the solid phase is prepared in the container. It is efficient that the glycoprotein fixed to the solid phase is prepared in the container, which is preferable.

(Container)

The container is not particularly limited as long as the container is capable of holding a liquid and a solid phase and separating the liquid (allowing the liquid to permeate) in a state of holding the solid phase, and examples of the container include each well of a column and a multi-well plate; each well of a filter plate; and a micro-tube. Further, the container may have a tube shape. Specifically, the container may have a tube shape with one end opened and the other end closed. The opened container is in a state in which the opening on one end side is not capped and the internal space and the external space of the container communicate with each other.

(Sugar Chain-Isolating Enzyme)

In the present embodiment, examples of the sugar chain-isolating enzyme include peptide N-glycanase (PNGase F and PNGase A) and endo-β-N-acetylglucosaminidase (Endo-H, Endo-F, Endo-A, and Endo-M).

The sugar chain-isolating enzyme may be prepared in a state of being dispersed in water or a buffer solution. In a case of using a buffer solution, examples of the buffer include ammonium carbonate, ammonium bicarbonate, ammonium chloride, diammonium hydrogen citrate, and ammonium carbamate. As the buffer solution, a buffer solution having a pH of 5 to 10 is preferable. In a case where the pH of the buffer solution is in the above-described range, the activity of a sugar chain-isolating enzyme is easily maintained. Water or the buffer solution may contain components such as a stabilizer of proteins such as salts such as metal salts, in addition to a sugar chain-isolating enzyme.

The isolation step may be performed in the presence of a deglycosylation promoter. In this manner, the recovery rate of the sugar chain-containing sample that contains a sugar chain isolated from the glycoprotein can be improved.

(Deglycosylation Promoter)

It is preferable that the deglycosylation promoter contains an acid-derived anionic surfactant. The protein portion of the glycoprotein is denatured so that the tertiary structure is changed by the acid-derived anionic surfactant and the sugar chain-isolating enzyme easily acts on a decomposition target site. In this manner, the sugar portion is easily decomposed and isolated.

The acid-derived anionic surfactant is an anionic surfactant derived from an organic acid. Examples thereof include a carboxylic acid type anionic surfactant, a sulfonic acid type anionic surfactant, a sulfuric acid ester type anionic surfactant, and a phosphoric acid ester type anionic surfactant. Among these, a carboxylic acid type anionic surfactant is preferable. In a case where the acid-derived anionic surfactant is a carboxylic acid type anionic surfactant, it is considered that the sugar chain-isolating enzyme is unlikely to be denatured while the protein portion of the glycoprotein is denatured.

Examples of the carboxylic acid type anionic surfactant include a carboxylic acid and a carboxylate represented by $R^1$—COOX (here, $R^1$ represents an organic group and X represents a hydrogen atom or a cation); and an amino acid and a salt thereof (N-acylamino acid surfactant) represented by $R^1CON(R^2)$—$R^3$—COOX (here, $R^1$ represents an organic group, —$N(R^2)$—$R^3$—COO— represents an amino acid residue, and X represents a hydrogen atom or a cation). Among these, an amino acid and a salt thereof (N-acylamino acid surfactant) represented by $R^1CON(R^2)$—$R^3$—COOX (here, $R^1$ represents an organic group, —$N(R^2)$—$R^3$—COO— represents an amino acid residue, and X represents a hydrogen atom or a cation) are preferable.

Examples of the cation X include alkali metal ions such as sodium or potassium, a triethanolamine ion, and an ammonium ion. Further, in all examples of the acid-derived anionic surfactants described below, the "salt" is intended to exemplify at least a sodium salt, a potassium salt, a triethanolamine salt, or an ammonium salt.

In the carboxylate represented by $R^1$—COOX, the organic group $R^1$ represents a group having at least carbon, and examples thereof include a higher alkyl group, a higher unsaturated hydrocarbon group, a hydrocarbon group having an oxyalkylene group interposed therein, and a fluorine-substituted higher alkyl group.

The number of carbon atoms of the higher alkyl group or the higher unsaturated hydrocarbon group may be in a range of 6 to 18. Specific examples of the carboxylic acid type anionic surfactant containing such a higher alkyl group or higher unsaturated hydrocarbon group include an octanoate, a decanoate, a laurate, a myristate, a palmitate, a stearate, an oleate, and a linoleate. Further, the above-described higher alkyl group or higher unsaturated hydrocarbon group may be substituted, and the substituent may be an alkyl group or alkoxycarbonyl group having 1 to 30 carbon atoms.

In the hydrocarbon group having an oxyalkylene group interposed therein, one or more oxyalkylene groups may be included in the main chain thereof. Examples of the oxyalkylene group include an oxyethylene group, an oxy-n-propylene group, and an oxyisopropylene group. As the hydrocarbon group having an oxyalkylene group interposed therein, a group represented by $R^4$—$(CH_2CH_2O)_n$—$R^5$— may be exemplified.

Here, $R^4$ may represent a higher alkyl group, a higher unsaturated hydrocarbon group, or a substituted or unsubstituted aryl group. The number of carbon atoms of the higher alkyl group or the higher unsaturated hydrocarbon group may be in a range of 6 to 18. Examples of the aryl group include a phenyl group and a naphthyl group. In a case of a substituted aryl group, the substituent may be a linear or branched alkyl group, and the number of carbon atoms of the linear or branched alkyl group may be in a range of 1 to 30. Particularly in a case of a phenyl group, the substituent may be substituted at the para position with respect to a sulfonyl group. Further, n may represent a number of 1 to 10. $R^5$ may represent a sigma bond or an alkylene group such as an ethylene group, a methylene group, or an n-propylene group. Specific examples of such a carboxylate include a laureth carboxylate (such as laureth-4-carboxylate or laureth-6-carboxylate) and a trideceth carboxylate (such as trideceth-4-carboxylate or trideceth-6-carboxylate).

In the fluorine-substituted higher alkyl group, one or more hydrogen atoms are substituted with a fluorine atom. The fluorine-substituted higher alkyl group may be perfluoroalkyl group in which all hydrogen atoms are substituted with fluorine. Further, the carbon atoms thereof may be in a range of 6 to 18. Specific examples of the perfluoroalkylcarboxylic acid and the perfluoroalkylcarboxylate include perfluorooctanoic acid, perfluorononanoic acid, perfluorooctanoate, and perfluorononanoate.

In the amino acid and the salt thereof contained in the carboxylic acid type anionic surfactant, in the amino acid and the salt thereof represented by $R^1CON(R^2)$—$R^3$—COOX, the organic group $R^1$ and the cation X have the same definitions as those for the organic group $R^1$ and the cation X in the carboxylic acid or the carboxylate described above.

Further, $R^2$ represents a hydrogen atom or an alkyl group (such as a methyl group, an ethyl group, an n-propyl group, or an isopropyl group). $R^3$ may represent a substituted or unsubstituted ethylene group, methylene group, or n-propylene group and may form a ring together with nitrogen atoms on the N-terminal side. Accordingly, the amino acid residue represented by —$N(R^2)$—$R^3$—COO— may be an α-amino acid residue, a β-amino acid residue, a γ-amino acid residue, a residue derived from a natural amino acid, or a residue derived from an unnatural amino acid. Examples thereof include residues derived from an amino acid such as a sarcosine residue, a glutamic acid residue, a glycine residue, an aspartic acid residue, a proline residue, and a β-alanine residue.

Specific examples of the amino acid or the salt thereof (that is, a N-acylamino acid surfactant) in a case where $R^2$ represents a hydrogen atom include N-lauroyl aspartate, N-lauroyl glutamic acid, N-lauroyl glutamate, N-myristoyl glutamate, N-cocoylalanine salt, N-cocoylglycine salt, N-cocoyl glutamate, N-palmitoyl glutamate, N-palmitoyl proline, N-palmitoyl proline salt, N-undecylenoyl glycine, N-laudecylenoyl glycine salt, and N-stearoyl glutamine salt. In a case where the acid-derived anionic surfactant is a N-acylamino acid surfactant, there is a tendency that the protein portion of the glycoprotein is easily denatured and the sugar chain-isolating enzyme is unlikely to be denatured.

Specific examples of the amino acid or the salt thereof in a case where $R^2$ represents an alkyl group (in other words, a N-acyl-N-alkylamino acid surfactant) include N-cocoyl-N-methylalanine, N-cocoyl-N-methylalanine salt, N-myristoyl-N-methyl-β-alanine, N-myristoyl-N-methyl-β-alanine salt, N-myristoyl sarcosine salt, N-lauroyl-N-methylalanine, N-lauroyl-N-methylalanine salt, N-lauroyl-N-ethylglycine, N-lauroyl-N-isopropylglycine salt, N-lauroyl-N-methyl-β-alanine, N-lauroyl-N-methyl-β-alanine salt, N-lauroyl-N-ethyl-β-alanine, N-lauroyl-N-ethyl-β-alanine salt, N-lauroyl sarcosine, N-lauroyl sarcosine salt, N-cocoyl sarcosine, N-cocoyl sarcosine salt, N-oleoyl-N-methyl-β-alanine, N-oleoyl-N-methyl-β-alanine salt, N-oleoyl sarcosine, N-oleoyl sarcosine salt, N-linoleyl-N-methyl-β-alanine, N-palmitoyl-N-methyl-β-alanine, and N-palmitoyl sarcosine salt. In a case where the acid-derived anionic surfactant is a N-acyl-N-alkylamino acid surfactant, there is a tendency that the protein portion of the glycoprotein is more easily denatured and the sugar chain-isolating enzyme is unlikely to be denatured.

The sulfonic acid type anionic surfactant is a sulfonic acid or a sulfonate represented by $R^1$—$SO_3X$ (here, $R^1$ represents an organic group and X represents a hydrogen atom or a cation). The organic group $R^1$ represents a group having at least carbon, and examples of the organic group include a higher alkyl group, a higher unsaturated hydrocarbon group, a hydrocarbon group having an oxyalkylene group interposed therein, a fluorine-substituted higher alkyl group, a substituted or unsubstituted aryl group, and a higher alkyl group or higher unsaturated hydrocarbon group having a divalent linking group (such as —O—, —CO—, —CONH—, or —NH—) interposed therein.

The higher alkyl group, the higher unsaturated hydrocarbon group, the hydrocarbon group having an oxyalkylene group interposed therein, the fluorine-substituted higher alkyl group, and the cation X among the examples of the organic group $R^1$ have the same definitions as those for the organic group $R^1$ and the cation X in the carboxylic acid or the carboxylate.

Specific examples thereof include 1-hexanesulfonate, 1-octanesulfonate, 1-decanesulfonate, and 1-dodecanesulfonate; perfluorobutanesulfonate, perfluorobutanesulfonate, perfluorooctanesulfonate, and perfluorooctanesulfonate; tetradecenesulfonate; and an alpha sulfo fatty acid methyl ester salt ($CH_3(CH_2)_nCH(SO_3X)COOCH_3$) (n represents an integer of 1 to 30).

In a case where the organic group $R^1$ represents a substituted or unsubstituted aryl group, examples of the aryl group include a phenyl group and a naphthyl group. In a case of a substituted aryl group, the substituent may be a linear or branched alkyl group and the number of carbon atoms of the linear or branched alkyl group may be in a range of 1 to 30. Particularly in a case of a phenyl group, the substituent may be substituted at the para position with respect to a sulfonyl group. Examples of such an aromatic sulfonate include a toluene sulfonate, a cumene sulfonate, an octyl benzene sulfonate, a dodecyl benzene sulfonate, a naphthalene sulfonate, a naphthalene disulfonate, a naphthalene trisulfonate, and a butyl naphthalene sulfonate.

Examples of the sulfonic acid type surfactant in a case where the organic group $R^1$ represents a higher alkyl group or higher unsaturated hydrocarbon group having a divalent linking group (such as —O—, —CO—, —CONH—, or —NH—) interposed therein include an isethionate which is O-substituted with the higher alkyl group or higher unsaturated hydrocarbon group; and a taurine salt which is N-substituted with the higher alkyl group or higher unsaturated hydrocarbon group. The number of carbon atoms of the higher alkyl group or higher unsaturated hydrocarbon group may be in a range of 6 to 18. Specific examples of such a sulfonic acid type surfactant include a cocoyl isethionate, a cocoyl taurine salt, cocoyl-N-methyl taurine, N-oleoyl-N-methyl taurine salt, N-stearoyl-N-methyl taurine salt, and N-lauroyl-N-methyl taurine salt.

The sulfuric acid ester type anionic surfactant is a sulfuric acid ester salt represented by $R^1$—$OSO_3X$ (here, $R^1$ represents an organic group and X represents a cation). The organic group $R^1$ represents a group having at least carbon, and examples thereof include a higher alkyl group, a higher unsaturated hydrocarbon group, a hydrocarbon group having an oxyalkylene group interposed therein, and a fluorine-substituted higher alkyl group. These groups have the same definitions as those for $R^1$ in the carbon type surfactant described above. Examples of the cation X include an alkali metal ion such as sodium or potassium, a triethanolamine ion, and an ammonium ion.

Specific examples of the sulfuric acid ester salt include a lauryl sulfate, a myristyl sulfate, a laureth sulfate ($C_{12}H_{25}(CH_2CH_2O)_nOSO_3X$, here, n represents an integer of 1 to 30), and sodium polyoxyethylene alkyl phenol sulfonate ($C_8H_{17}C_6H_4O[CH_2CH_2O]_3SO_3X$).

The phosphoric acid ester type anionic surfactant is a phosphoric acid ester or a phosphoric acid ester salt represented by $R^1$—$OSO_3X$ (here, R1 represents an organic group and X represents a hydrogen atom or a cation). The organic group R represents a group having at least carbon, and examples thereof include a higher alkyl group, a higher unsaturated hydrocarbon group, a hydrocarbon group having an oxyalkylene group interposed therein, and a fluorine-substituted higher alkyl group. These groups have the same definitions as those for $R^1$ in the carbon type surfactant described above. Examples of the cation X include an alkali metal ion such as sodium or potassium, a triethanolamine ion, and an ammonium ion.

Specific examples of the phosphoric acid ester or phosphoric acid ester salt include lauryl phosphoric acid and lauryl phosphate.

The deglycosylation promoter may be prepared in a state in which the acid-derived anionic surfactant is dissolved or dispersed in water or a buffer solution. In a case of using a buffer solution, examples of the buffer include ammonium salts such as ammonium carbonate, ammonium bicarbonate, ammonium chloride, diammonium hydrogen citrate, and ammonium carbamate; a tris buffer such as trishydroxymethylammonium; and a phosphate. As the buffer solution, a buffer solution having a pH of 5 to 10 is preferable. In a case where the pH of the buffer solution is in the above-described range, the activity of a sugar chain-isolating enzyme is easily maintained. Examples of components other than the acid-derived anionic surfactant contained in water or the buffer solution in the deglycosylation promoter include salts such as metal salts other than surfactants.

In the isolation step according to the present embodiment, an isolating reaction solution containing a glycoprotein and a sugar chain-isolating enzyme, in which the optimum conditions (the temperature and the pH) for the sugar chain-isolating enzyme are satisfied may be prepared.

In a case of using a deglycosylation promoter, an isolating reaction solution in which the optimum conditions (the temperature, the pH, and the like) of the sugar chain-isolating enzyme are satisfied and which contains a glycoprotein, an acid-derived anionic surfactant, and a sugar chain-isolating enzyme may be prepared. Therefore, in the case of using a deglycosylation promoter, a sample containing a fixed glycoprotein (hereinafter, also simply referred to as a sample containing a glycoprotein), a deglycosylation promoter, and a sugar chain-isolating enzyme may be mixed in any operation procedure.

For example, the sample containing the glycoprotein, the deglycosylation promoter, and the sugar chain-isolating enzyme were mixed with each other at the same timing to prepare an isolating reaction solution. Further, the isolating reaction solution may be prepared by adding the deglycosylation promoter and then adding the sugar chain-isolating enzyme. Further, in a case where the glycoprotein fixed to the solid phase is obtained by performing a pre-treatment described below and the deglycosylation promoter and the surfactant used for the pre-treatment are formed of the same substance, the surfactant in an amount corresponding to the amount of the deglycosylation promoter is added to the surfactant in an amount corresponding to the amount of a pre-treatment agent and then added in advance during the pre-treatment, and then only the sugar chain-isolating enzyme may be added during the isolation step (because of the state in which the deglycosylation promoter is already present).

Specifically, the isolating reaction solution into which all components are mixed is prepared, the optimum temperature are set, and then a reaction of isolating the sugar chain from the glycoprotein can be carried out. In this case, the reaction time may be in a range of 5 seconds to 24 hours.

In a case of using the deglycosylation promoter, the sample containing the glycoprotein and the acid-derived anionic surfactant may be mixed with each other in advance so that the protein portion of the glycoprotein is denatured and then the mixture may be mixed with the sugar chain-isolating enzyme. In this case, the denaturation time may be in a range of 5 seconds to 24 hours and the sugar chain-isolation time may be in a range of 5 seconds to 24 hours.

In the isolating reaction solution, the concentration of the glycoprotein may be in a range of 0.1 µg/mL to 100 mg/mL or in a range of 1 µg/mL to 10 mg/mL. It is preferable that the concentration of the glycoprotein in the isolating reaction solution is greater than or equal to the above-described lower limit from the viewpoint of detectability. It is preferable that the concentration thereof is less than or equal to the above-described upper limit from the viewpoint of quantitativity.

In a case of using the deglycosylation promoter, the concentration of the acid-derived anionic surfactant in the isolating reaction solution may be in a range of 0.01% to 30% by mass, in a range of 0.2% to 1.0% by mass, in a range of 0.2% to 0.3% by mass, or in a range of 0.22% to 0.27% by mass. Alternatively, the amount of the acid-derived anionic surfactant may be set to be in a range of 0.001 µg to 100 mg or less with respect to 1 µg of the glycoprotein.

By setting the amount of the acid-derived anionic surfactant to be used to be in the above-described range, the activity of the sugar chain-isolating enzyme is maintained, the recovery amount of the isolated sugar chain becomes excellent, and the stability of the recovery amount also becomes excellent. Further, it is preferable that the purification of the isolated sugar chain is performed by a solid phase carrier from the viewpoint of preventing the drying time from being excessively long.

The concentration of the sugar chain-isolating enzyme in the isolating reaction solution may be in a range of 0.001 µU/mL to 1000 mU/mL or in a range of 0.01 µU/mL to 100 mU/mL. Alternatively, the amount of the sugar chain-isolating enzyme may be set to be in a range of 0.001 µU to 1000 mU with respect to 1 µg of the glycoprotein. In a case where the amount of the sugar chain-isolating enzyme to be used is in the above-described range, the sugar chain can be efficiently isolated.

The reaction pH may be adjusted to the optimum pH of the sugar chain-isolating enzyme and may be in a range of 5 to 10. The reaction temperature may be adjusted to the optimum temperature of the sugar chain-isolating enzyme and may be in a range of 4° C. to 90° C.

In the isolation step, the reaction time varies depending on the scale or the like of the glycoprotein and may be in a range of 5 seconds to 24 hours. It is preferable that the reaction system of the isolation step is made to be an open system (for example, a state in which the container is opened) and heated so that the solvent is evaporated. Further, after the container is heated in a closed (capped) state, the solvent in the container in an opened state may be dried and removed according to a known method. The heating temperature may be higher than or equal to 40° C. or higher than or equal to 45° C. In this manner, since the solvent during the isolation step is evaporated and the concentration of the reaction solution gradually increases, it is easy to set the concentration of the reaction solution to the extent that the isolation of the sugar chain efficiently proceeds regardless of the scale of the glycoprotein provided for the method of the present embodiment. Further, since solvent removal is performed together with the isolation reaction, the time for performing the solvent removal step separately from the isolation step is shortened or becomes unnecessary so that it becomes possible to rapidly prepare a sugar chain. The upper limit of the heating temperature may be, for example, 80° C. from the viewpoint of preventing denaturation of the sugar chain-isolating enzyme.

In this manner, a sugar chain-containing sample that contains a sugar chain separated from the glycoprotein in the sample is obtained by performing the isolation step.

<Pre-Treatment Step>

As an example of the method for preparing a sugar chain of the present embodiment, the method may further include a pre-treatment step of bringing a pre-treatment agent that contains a surfactant or a chaotropic reagent, for example, urea and guanidine salts such as guanidine chloride, guanidine thiocyanate, or guanidine hydrochloride into contact with the sample before the isolation step.

In this manner, the sugar chain can be easily isolated from the glycoprotein without performing a decomposition treatment on the protein portion. As the result, the time taken for the sugar chain-isolating treatment can be greatly shortened.

In the pre-treatment step, a pre-treatment agent containing a surfactant is brought into contact with the sample containing the glycoprotein fixed to the solid phase. The pre-treatment step may be performed after the capturing of the glycoprotein is completed by bringing the sample containing the glycoprotein into contact with the solid phase, after the solid phase synthesis is completed, or after the cleaning treatment is performed and before the glycoprotein is brought into contact with the sugar chain-isolating enzyme. By performing the pre-treatment step, the sugar chain-isolating enzyme easily acts on the glycoprotein in the isolation step.

The surfactant contained in the pre-treatment agent may be any of an anionic surfactant, a cationic surfactant, an amphoteric surfactant, and a non-ionic surfactant.

The anionic surfactant is not particularly limited, and examples thereof include a salt of fatty acid such as soap, an alkyl benzene sulfonate, a higher alcohol sulfuric acid ester salt, a polyoxyethylene alkyl ether sulfate, α-sulfofatty acid ester, α-olefin sulfonate, a monoalkyl phosphoric acid ester salt, and an alkyl sulfonate. However, it is preferable that the anionic surfactant is an anionic surfactant which can be used as a deglycosylation promoter used in the sugar chain isolation step described below (in the present specification, the anionic surfactant which can be used as a deglycosylation promoter is particularly referred to as an acid-derived anionic surfactant). In a case where the acid-derived anionic surfactant is used in the pre-treatment step, the surfactant may be a surfactant which is the same as or different from the surfactant exemplified as a deglycosylation promoter used in the sugar chain isolation step.

The cationic surfactant is not particularly limited, and examples thereof include an alkyl trimethyl ammonium salt, a dialkyl dimethyl ammonium salt, an alkyl dimethyl benzyl ammonium salt, and an amine salt. The amphoteric surfactant is not particularly limited, and examples thereof include an alkylamino fatty acid salt, alkyl betaine, and alkylamine oxide. The non-ionic surfactant is not particularly limited, and examples thereof include polyoxyethylene alkyl ether, polyoxyethylene alkyl phenyl ether, alkyl glucoside, polyoxyethylene fatty acid ester, sucrose fatty acid ester, sorbitan fatty acid ester, polyoxyethylene sorbitan fatty acid ester, fatty acid alkanolamide, and a polyoxyethylene-polyoxypropylene block copolymer.

The pre-treatment agent may be used in a state in which the surfactant is dissolved in water or a buffer solution. In a case of using a buffer solution, examples of the buffer include ammonium salts such as ammonium carbonate, ammonium bicarbonate, ammonium chloride, diammonium hydrogen citrate, and ammonium carbamate; a tris buffer such as trishydroxymethylammonium; and a phosphate. As the buffer solution, a buffer solution having a pH of 5 to 10 is preferable. In a case where the pH of the buffer solution is in the above-described range, the activity of a sugar chain-isolating enzyme used in the subsequent step is easily maintained. In the sample containing the glycoprotein, examples of components other than the glycoprotein contained in water or the buffer solution include a stabilizer of proteins, for example, salts such as metal salts.

The concentration of the surfactant in the pre-treatment agent may be in a range of 0.01% to 30% by mass, in a range of 0.2% to 1.0% by mass, in a range of 0.2% to 0.3% by mass, or in a range of 0.22% to 0.27% by mass. In a case where the concentration thereof is greater than or equal to the above-described lower limit or the concentration thereof is less than or equal to the above-described upper limit, the sugar chain isolated in the subsequent sugar chain isolation step can be obtained at a high recovery rate.

The pre-treatment agent can be separated from the glycoprotein fixed to the solid phase after being brought into contact with the solid phase. The separation may be performed at once after all of a predetermined amount of pre-treatment agent to be used is put into a container or the separation may be performed whenever a part of the predetermined amount of pre-treatment agent is put into the container several times. The separation of the pre-treatment agent can be performed by reducing the pressure, performing centrifugation, or the like.

The glycoprotein fixed to the solid phase on which the pre-treatment step has been performed may be provided for the isolation step without performing cleaning from the viewpoint of rapid preparation. However, a cleaning operation may be performed after the pre-treatment step and before the isolation step. The cleaning operation may be appropriately performed between operations.

<Labeling Step>

As an example of the method for preparing a sugar chain of the present embodiment, the method includes a labeling step of adding a labeling reagent to a sugar chain-containing sample which contains a sugar chain to obtain a labeled product containing a labeled substance of the sugar chain. In the labeling step, the reaction between the labeling reagent and the sugar chain can be carried out in a container. Further, the labeling step may be performed using the same container as the container in which the isolation step has been performed.

In the labeling step, the labeled product containing a labeled substance of a sugar chain can be obtained by adding a labeling reagent (labeling reaction solution) containing a labeling reagent containing a labeled compound to the sugar chain-containing sample that contains a sugar chain in the container obtained in the isolation step.

(Labeled Compound)

The labeled compound is not particularly limited as long as the labeled compound contains a reactive group with respect to a sugar chain and a modifying group to be attached to the sugar chain. Examples of the reactive group with respect to a sugar chain include an oxylamino group, a hydrazide group, and an amino group. The modifying group can be appropriately selected by those skilled in the art according to the method of analyzing a sugar chain.

For example, in a case where the labeled compound includes an oxylamino group or a hydrazide group as a reactive group with respect to a sugar chain, as the modifying group to be attached to the sugar chain, an amino acid residue selected from the group consisting of an arginine residue, a tryptophan residue, a phenylalanine residue, a tyrosine residue, a cysteine residue, and a lysine residue can be selected.

It is preferable that the labeled compound contains an arginine residue from the viewpoints of promoting ionization at the time of MALDITOF-MS measurement of the modified sugar chain and improving the detection sensitivity. It is preferable that the labeled compound contains a tryptophan residue from the viewpoints of improving the separability and improving the fluorescence detection sensitivity at the time of reversed phase HPLC detection of the modified sugar chain because the tryptophan residue is fluorescent and hydrophobic. It is preferable that the labeled compound contains a phenylalanine residue and/or a tyrosine residue from the viewpoint of being suitable for detection using UV absorption of the modified sugar chain. In a case where the labeled compound contains a cysteine residue, labeling with a labeling reagent such as an ICAT reagent (Applied Biosystems, USA) can be made using a —SH group of the residue as a target. In a case where the labeled compound contains a lysine residue, labeling with a labeling reagent such as an iTRAQ reagent (Applied Biosystems, USA) and an ExacTag reagent (Perkin Inc., USA) can be made using an amino group of the residue as a target. In a case where the labeled compound contains a tryptophan residue, labeling with an NBS reagent (Shimadzu Corporation, Japan) can be made using an indole group of the residue as a target.

For example, in a case where the labeled compound contains an amino group as a reactive group with respect to the sugar chain, a compound that contains an amino group having UV absorption characteristics or fluorescence characteristics can be used as the labeled compound. In the compound containing this amino group, an aromatic group may be exemplified as a modifying group to be attached to the sugar chain. When the labeled compound containing an amino group and an aromatic group is used, modification is performed by reductive amination. Since the aromatic group has UV absorption characteristics or fluorescence characteristics, the detection sensitivity at the time of UV detection or fluorescence detection is improved, which is preferable.

Specific examples of the labeled compound that provides such an aromatic group include 8-aminopyrene-1,3,6-trisulfonate, 8-aminonaphthalene-1,3,6-trisulphonate, 7-amino-1,3-naphtalenedisulfonic acid, 2-amino9(10H)-acridone, 5-aminofluorescein,dansylethylenediamine, 2-aminopyridine, 7-amino-4-methylcoumarine, 2-aminobenzamide, 2-aminobenzoic acid, 3-aminobenzoic acid, 7-amino-1-naphthol, 3-(acetylamino)-6-aminoacridine, 2-amino-6-cyanoethylpyridine, ethyl p-aminobenzoate, p-aminobenzonitrile, and 7-aminonaphthalene-1,3-disulfonic acid.

Among these, the compound containing an amino group may contain 2-aminobenzamide. 2-aminobenzamide is preferable from the viewpoint that 2-aminobenzamide is relatively unlikely to be affected by impurities (for example, salts, proteins, and other biological molecules) even in a case where the reaction scale is large. In addition, the method of the present embodiment is particularly useful in a case where the reaction scale is small. Since 2-aminobenzamide is unlikely to be affected by impurities as the reaction scale is small, 2-aminobenzamide can be applied to various labeling reagents (labeling reaction solutions). Further, derivatives of the above-described compounds are also preferably used as long as the functions of the labeled compound are maintained.

The labeled compound can be used by being dissolved in water, a buffer solution, and/or an organic solvent. Examples of the buffer solution include the aqueous solutions of the buffers which are the same as those used in the isolation step.

(Labeling Reagent)

The labeling reagent of the present embodiment may contain a labeled compound such as a compound containing an amino group with UV absorption characteristics or fluorescence characteristics, a reducing agent, and an organic solvent.

The organic solvent may contain one or more selected from the group consisting of an aprotic polar organic solvent, a protic polar organic solvent, and an aprotic non-polar organic solvent.

Specific examples of the buffer solution include the aqueous solutions of the buffers which are the same as those used in the isolation step described above. Examples of the organic solvent include an aprotic polar organic solvent such as dimethyl sulfoxide (DMSO), dimethylformamide (DMF), or N-methylpyrrolidone (NMP); a protic polar organic solvent such as an organic acid (formic acid, acetic acid, propionic acid, or butyric acid) or alcohol (methanol, ethanol, or propanol); and an aprotic non-polar organic solvent such as hexane. These solvents may be used alone or in combination of two or more kinds thereof.

From the viewpoint of more preferably obtaining the effects of shortening the time required for the labeling step, an organic acid such as formic acid, acetic acid, propionic acid, or butyric acid can be used as the organic solvent. Among these, from the viewpoint of ease of an operation, it is preferable that the organic acid is acetic acid.

In a case where the boiling point of the protic polar organic solvent is relatively low (for example, in a case where the boiling point thereof is lower than 140° C.), in addition to a protic solvent, a solvent having a boiling point higher than that of the protic solvent may be used in combination. In this manner, the volatilization rate of the protic polar organic solvent having a relatively low boiling point in the labeling step. As the result, undesired precipitation of an unreacted substance can be suppressed during the labeling step. In this manner, the labeled sugar chain can be obtained with excellent yield. The form of using a solvent having a high boiling point (hereinafter, a high-boiling point solvent) together can be selected in a case where the scale of the sugar chain is small, a case where the amount of solvent is small, and/or a case where the reaction time becomes longer.

As the above-described high-boiling point solvent, for example, an aprotic polar organic solvent having a boiling point of 140° C. to 200° C. may be used. Specific examples of the high-boiling point solvent include an aprotic polar organic solvent such as dimethyl sulfoxide, dimethylformamide, and N-methylpyrrolidone.

In a case where an aprotic polar organic solvent is used in combination as a high-boiling point solvent, the high-boiling point solvent is preferably used in an amount of lower % by volume than that of the protic polar organic solvent, may be greater than or equal to 4% by volume and less than 100% by volume of the protic polar organic solvent, or may be 4% to 70% by volume of the protic polar organic solvent, from the viewpoints of improving the solubility and reactivity of 2-aminobenzamide serving as the labeled compound and the reducing agent.

In the modification performed by reductive amination, efficient labeling can be carried out by allowing an aldehyde group formed at a reducing terminal of the sugar chain to react with an amino group of the labeled compound and reducing the formed Schiff base using a reducing agent so that a modifying group is introduced into the reducing terminal of the sugar chain.

As the reducing agent, the labeling reagent may include one or more selected from the group consisting of sodium cyanoborohydride, sodium triacetoxyborohydride, methylamine borane, dimethylamine borane, trimethylamine borane, picoline borane, and pyridine borane. By using picoline borane with low toxicity, labeling with high safety can be performed.

From the viewpoints of safety and reactivity, it is preferable to use picoline borane (2-picoline-borane). From the same viewpoint, in a case where picoline borane is used as a reducing agent, it is preferable to use 2-aminobenzamide as the labeled compound. In the case where picoline borane is used as a reducing agent, it is preferable that a protic polar organic solvent is included as a solvent. In this manner, since picoline borane can be dissolved at a high concentration, the time required for the labeling step is shortened. As the solvent, a mixed solvent of a protic polar organic solvent such as acetic acid and an aprotic polar organic solvent such as dimethyl sulfoxide may be used.

In the labeling step of the present embodiment, the reaction environment of the labeling reagent and the sugar chain contained in the sugar chain-containing sample contains water. Specifically, in the labeling step, the labeling reagent can react with the sugar chain in a state in which the reaction environment in the container contains water. In this manner, as described above, the labeling efficiency can be increased.

In the labeling step, the reaction environment of the labeling reagent and the sugar chain may be present in a solid phase, but the present invention is not limited thereto. For example, the reaction environment may be present in a liquid phase on the bottom surface of the container without being present in a solid phase. This reaction environment system may be formed of a labeled compound, a labeling reagent containing a reducing agent and an organic solvent, a sugar chain-containing sample containing a sugar chain, and water. The liquid phase may be formed of a solvent and the like in the reaction environment system.

In the labeling step, in a case where the amount of the moisture in the reaction environment is set as X ($\mu$L) and the amount of the sugar chain therein is set as Y ($\mu$g), the lower limit of X/Y representing the ratio of the moisture amount to the sugar chain amount is, for example, greater than or equal to 1.2, preferably greater than or equal to 1.3, and more preferably greater than or equal to 2. In this manner, by setting X/Y representing the ratio of the moisture amount to the sugar chain amount to be greater than or equal to the lower limit, the sugar chain labeling can be efficiently performed. Further, labeling on a sugar chain that is present in the reaction environment at a high concentration (for example, greater than 1 $\mu$g) can be stably performed. The upper limit of X/Y is preferably less than or equal to 50 and more preferably less than or equal to 30. By setting X/Y to be less than or equal to the upper limit, the concentration of the labeled compound in the reaction environment is decreased due to the excessive amount of water, and thus a decrease in labeling efficiency can be suppressed.

In the labeling step, from the viewpoint of stably performing labeling on the sugar chain that is present in the reaction environment at a high concentration greater than or equal to a predetermined concentration, the labeling efficiency and the labeling properties can be improved by appropriately controlling the reaction environment of the sugar chain and the labeling reagent such that the moisture amount is set to be greater than the sugar chain amount. The lower limit of X/Y indicates that the moisture amount is greater than the sugar chain amount.

Further, a decrease in labeling efficiency can be suppressed by appropriately controlling the reaction environment of the sugar chain and the labeling reagent such that the concentration of the labeled compound in the reaction environment is not extremely decreased due to the excessive amount of water. The upper limit of X/Y indicates the moisture amount in which the concentration of the labeled compound does not extremely decrease.

In the small scale in the labeling step of the present embodiment, the sugar chain labeling can be performed even in a case where a trace amount of water is present. In other words, in a case where the amount of the sugar chain in the reaction environment is greater than 0 μg and less than 1 μg in the labeling step, the amount of water in the reaction environment is, for example, greater than 0 μL and less than or equal to 1.0 μL, preferably less than or equal to 0.5 μL, and more preferably less than or equal to 0.3 μL. In this manner, the labeling efficiency with respect to the sugar chain that is present in the reaction environment at a low concentration can be improved even with a trace amount of water.

In the labeling step with the small scale, the condition of the sugar chain that is present at a low concentration is represented by a sugar chain amount of greater than 0 μg and less than 1 μg, and the condition of a trace amount of water is represented by a water amount of greater than 0 μL and equal to or less than 1.0 μL. At this time, the sugar chain amount may be greater than 0 μg and less than 1 μg, greater than 0 μg and equal to or less than 0.9 μg, or greater than 0 μg and equal to or less than 0.8 μg.

Here, Non-Patent Document 2 (a guide for a glycan labeling kit obtained by using 2-AB) describes that the dried sample is re-dissolved in 10 μl of water, but there is no description on the technical relationship between the sugar chain amount on a weight basis and the water amount on a volume basis. Further, since it is a matter of choosing a sample, from among samples with different kinds of glucan and with different weights, to be optionally determined by a user of the kit, Non-Patent Document 2 which is a guide for the kit has no specific description on conditions for these issues.

In the labeling step of the present embodiment, the amount of water in the reaction environment can be appropriately adjusted by adding water after the solvent containing water in the sugar chain-containing sample has been completed removed before the labeling step, removing some of the solvent before the labeling step so that water remains, or using the water contained in the labeling reagent during the addition of the labeling reagent that contains a labeled compound or a reducing agent.

In other words, according to the method of the present embodiment, a step of adding water into the reaction environment can be performed in the labeling step. At this time, water may be removed by completely drying the water-containing solvent in the sugar chain-containing sample or at least some water may be removed by semi-drying the solvent before addition of water. Specifically, the solvent can be dried using a method of performing heating, suctioning, or centrifugation in a state in which the container is opened. In this manner, the reaction environment during the labeling step can contain water.

The method of the present embodiment may include a step of removing at least some of the water-containing solvent in the sugar chain-containing sample before the labeling step. At this time, some of the water-containing solvent can be allowed to remain without being completely removed before the labeling step. In this manner, the reaction environment during the labeling step can contain water.

As an example of the method according to the present embodiment, the labeling reagent may be added to the sugar chain-containing sample in the labeling step in a state in which the container is opened or closed. At this time, the sugar chain-containing sample or the labeling reagent may be exposed to the external environment outside the container.

The reaction temperature in the labeling step may be in a range of 4° C. to 80° C. or in a range of 25° C. to 70° C. It is preferable that the reaction temperature is higher than or equal to the above-described lower limit from the viewpoint of shortening the reaction time. Further, it is preferable that the reaction temperature is lower than or equal to the above-described upper limit from the viewpoint of suppressing partial decomposition of the sugar chain due to a high temperature.

The reaction time in the labeling step may be in a range of 5 to 600 minutes or in a range of 30 minutes to 300 minutes. It is preferable that the reaction time is longer than or equal to the above-described lower limit from the viewpoint of quantitative labeling. Further, it is preferable that the reaction time is shorter than or equal to the above-described upper limit from the viewpoint of suppressing partial decomposition of the sugar chain.

Such a heat treatment may be performed using any container between a container in a state of an open system and a container in a state of a closed system.

By performing the above-described labeling step, the labeled product containing a labeled substance of a sugar chain can be obtained.

<Separation Step>

In a case where the labeled product obtained in the labeling step is present in a solid phase, the method may further include a separation step of performing solid-liquid separation after the labeling step to obtain a separate liquid containing the labeled sugar chain. In other words, the labeled substance of the sugar chain is eluted through the solid-liquid separation, the labeled substance of the sugar chain can be easily separated from the solid phase. For example, the labeled substance of the sugar chain can be eluted by liquid permeation of the eluent through the labeled product. The eluent used in this case may be a water-based solution such as water, an aqueous solution, or a colloidal solution. As the eluent, a solution having a property of cutting ability with respect to the bond between the solid phase and the protein portion may be selected (in a case where the labeled sugar chain is analyzed by chromatography) or a solution which does not have such a property may be selected (a case where the labeled sugar chain is analyzed by mass analysis). In this manner, a separate liquid containing a labeled substance of the sugar chain is obtained.

Further, the separation step may be performed after the isolation step and before the labeling step. In this manner, the sugar chain-containing sample containing a sugar chain can be eluted to the bottom of the container by performing solid-liquid separation.

<Purification Step>

The method of the present embodiment may include a purification step. Depending on the method of analyzing the sugar chain, the labeled sugar chain may be purified by removing unnecessary substances from the separate liquid. The unnecessary substances may be removed by liquid permeation of the separate liquid through the solid phase for purification, capturing the labeled substance of the sugar chain, and re-eluting the captured labeled substance of the sugar chain. Further, the purification step may be performed between steps such as the pre-treatment step, the isolation step, the separation step, and the labeling step without limitation to the timing after the separation step.

In a case where the excess labeled compound used in the labeling step and the deglycosylation promoter used in the isolation step are used together with the labeled substance of the sugar chain, unnecessary substances such as the acid-derived anionic surfactant are present in the separate liquid. In a case where a solution having cutting ability with respect to the bond between the solid phase and the protein portion is selected as the eluent, proteins are mixed into the separate liquid. In such a case, the above-described purification step can be performed. In a case where a solution which does not have cutting ability with respect to the bond between the solid phase and the protein portion is selected as the eluent, proteins are not substantially contained in the separate liquid.

Further, known treatments such as cleaning or centrifugation other than the above-described purification can be appropriately performed between steps or before or after the pre-treatment step, the isolation step, the separation step, and the labeling step.

<Analyzing Step>

The labeled substance of the sugar chain prepared by the method of the present embodiment can be analyzed qualitatively and/or quantitatively using a known method such as a mass analysis method (such as MALDI-TOF MS), chromatography (such as high performance liquid chromatography or HPAE-PAD chromatography), or electrophoresis (such as capillary electrophoresis). In the sugar chain analysis, various databases (for example, GlycoMod, Glycosuite, or SimGlycan (registered trademark)) can be used.

By means of the analysis of the glycoprotein sugar chain as described above, it becomes possible to accelerate research and development of antibody pharmaceutical products; sugar chain modification analysis of antibody pharmaceutical products which is performed during manufacture or quality assurance; analysis of glycoproteins in a specimen such as serum or the like which is performed during the retrieve and research of sugar chain biomarkers; sugar chain analysis of stem cells; analysis of sugar chains in an electrophoretic gel band; and sugar chain analysis of plant tissues.

The present invention is not limited to the above-described embodiments, and modifications, improvements, and the like within the range in which the object of the present invention can be achieved are included in the present invention.

Hereinafter, an example of a reference form will be added.

1. A method for preparing a sugar chain, including: a labeling step of adding a labeling reagent to a sugar chain-containing sample which contains a sugar chain to obtain a labeled product containing a labeled substance of the sugar chain, in which a reaction environment of the labeling reagent and the sugar chain contains water in the labeling step.

2. The method for preparing a sugar chain according to 1., in which, in a case where an amount of the water in the reaction environment is set as X (µL) and an amount of the sugar chain is set as Y (µg) in the labeling step, X/Y is greater than or equal to 1.2.

3. The method for preparing a sugar chain according to 1., in which, in a case where an amount of the sugar chain is greater than 0 µg and less than 1 µg in the labeling step, an amount of water in the reaction environment is greater than 0 µL and equal to less than 1.0 µL.

4. The method for preparing a sugar chain according to any one of 1. to 3., in which a reaction between the labeling reagent and the sugar chain is carried out in a container in the labeling step.

5. The method for preparing a sugar chain according to 4., in which the container has a tube shape.

6. The method for preparing a sugar chain according to any one of 1. to 5., further including: a step of removing at least some of a solvent contained in the sugar chain-containing sample before the labeling step.

7. The method for preparing a sugar chain according to 6., in which a step of adding water into the reaction environment is performed in the labeling step.

8. The method for preparing a sugar chain according to any one of 1. to 7., further including: an isolation step of acting a sugar chain-isolating enzyme on a sample in a state of being fixed to a solid phase to obtain the sugar chain-containing sample which contains the sugar chain, before the labeling step.

9. The method for preparing a sugar chain according to 8., in which the sugar chain-isolating enzyme contains peptide N-glycanase or endo-β-N-acetylglycosaminidase.

10. The method for preparing a sugar chain according to 8. or 9., in which the solid phase has a column or a cartridge structure.

11. The method for preparing a sugar chain according to any one of 8. to 10., further including: a separation step of performing solid-liquid separation after the isolation step to obtain a separate liquid which contains the sugar chain.

12. The method for preparing a sugar chain according to any one of 1. to 11., in which the labeling reagent contains a compound which contains an amino group having UV absorption characteristics or fluorescence characteristics, a reducing agent, and an organic solvent.

13. The method for preparing a sugar chain according to 12., in which the compound which contains an amino group contains 2-aminobenzamide.

14. The method for preparing a sugar chain according to 12. or 13., in which the reducing agent contains one or more selected from the group consisting of sodium cyanoborohydride, sodium triacetoxyborohydride, methylamine borane, dimethylamine borane, trimethylamine borane, picoline borane, and pyridine borane.

15. The method for preparing a sugar chain according to any one of 12. to 14., in which the organic solvent contains one or more selected from the group consisting of an aprotic polar organic solvent, a protic polar organic solvent, and an aprotic non-polar organic solvent.

16. The method for preparing a sugar chain according to any one of 1. to 15., in which the sugar chain is derived from a glycoprotein.

EXAMPLES

Hereinafter, the present invention will be described in detail with reference to examples. However, the present invention is not limited to the following examples.

Example 1

20 µL of a 2AM solution (a solution obtained by mixing 40 mg of 2-picoline borane, 80 mg of 2-aminobenzamide, 120 µL of acetic acid, and 40 µL of dimethyl sulfoxide (DMSO)) used as a labeling reagent and 1 µL of pure water were added to 0.3 µg of maltoheptaose (sugar chain: single oligosaccharide) dried with a centrifugal evaporator which was used as a sugar chain-containing sample to cause a reaction at 50° C. for 40 minutes. Acetonitrile was added to the obtained separate liquid containing a crude 2AB-labeled sugar chain, the solution was applied to the monolith silica spin column and cleaned, and the solution was eluted with 50 µL of pure water, thereby obtaining a separate liquid containing a purified 2AB-labeled sugar chain. Next, HPLC measurement was performed on the obtained 1 µL of separate liquid containing a purified 2AB-labeled sugar chain under the conditions listed in Table 2.

TABLE 1

| Column | | Waters ACQUITY UPLC BEH Glycan |
|---|---|---|
| Mobile phase | A solution | 0.1% formic acid, 40% acetonitrile aqueous solution |
| | B solution | 0.1% formic acid, 90% acetonitrile aqueous solution |
| Elution conditions | | B: 0% (0 minute) → B: 100% (20 minutes) |
| Flow rate | | 0.2 mL/min |
| Column temperature | | 40° C. |
| Detection | | Fluorescent detector (excitation wavelength of 320 nm, fluorescent wavelength of 400 nm) |

The A solution and the B solution of Table 1 were liquids respectively constituting a mobile phase, and the polarity of the mobile phase was adjusted by mixing the A solution and the B solution. Further, in Table 1, the description of "B: a % ($T_1$ min)→B: b % ($T_2$ min)" means that the concentration of the B solution was changed from a % to b % during ($T_2$–$T_1$) minutes. Here, $T_1$, $T_2$, a, and b each represent a real number. Further, "%" in Table 1 indicates % by volume.

The obtained HPLC spectrum is shown in FIG. 1(a). As shown in FIG. 1(a), it was confirmed that the 2AB-labeled sugar chain was detected. The values of the peak areas of the 2AB-labeled sugar chain are listed in Table 2.

Example 2

The procedures were the same as those in Example 1 except that the amount of pure water was changed to 4 µL. The results are listed in Table 2. Further, the obtained HPLC spectrum is shown in FIG. 1(b).

Example 3

The procedures were the same as those in Example 1 except that the amount of pure water was changed to 8 µL. The results are listed in Table 2. Further, the obtained HPLC spectrum is shown in FIG. 1(c).

Comparative Example 1

The procedures were the same as those in Example 1 except that pure water was not added. The results are listed in Table 2. Further, the obtained HPLC spectrum is shown in FIG. 1(d).

Example 4

The procedures were the same as those in Example 1 except that the amount of maltoheptaose was changed to 1 µg and the amount of pure water was changed to 4 µL. The results are listed in Table 2. Further, the obtained HPLC spectrum is shown in FIG. 2(a).

Example 5

The procedures were the same as those in Example 4 except that the amount of pure water was changed to 8 µL.

TABLE 2

| | Unit | Comparative Example 1 | Example 1 | Example 2 | Example 3 | Comparative Example 2 | Example 4 |
|---|---|---|---|---|---|---|---|
| Water amount X | µL | 0 | 1 | 4 | 8 | 0 | 4 |
| Sugar chain amount Y | µg | 0.3 | 0.3 | 0.3 | 0.3 | 1 | 1 |
| X/Y | | 0 | 3.3 | 13.3 | 26.7 | 0 | 4.0 |
| Peak area value | | 678625 | 923475 | 1091714 | 1180539 | 1504628 | 3191443 |
| Peak area ratio | | 1 | 1.36 | 1.61 | 1.74 | 1 | 2.12 |
| Labeling efficiency | | — | B | A | A | — | A |
| Peak area value ratio per sugar chain amount | | 1 | 1.36 | 1.61 | 1.74 | 0.67 | 1.41 |
| Labeling properties | | — | B | c | B | C | B |

| | Unit | Example 5 | Comparative Example 3 | Example 6 | Example 7 |
|---|---|---|---|---|---|
| Water amount X | µL | 8 | 0 | 4 | 8 |
| Sugar chain amount Y | µg | 1 | 3 | 3 | 3 |
| X/Y | | 8.0 | 0 | 1.3 | 2.7 |
| Peak area value | | 3622228 | 5734070 | 11472438 | 10434824 |
| Peak area ratio | | 2.41 | 1 | 2.00 | 1.82 |
| Labeling efficiency | | A | — | A | A |
| Peak area value ratio per sugar chain amount | | 1.60 | 0.84 | 1.69 | 1.54 |
| Labeling properties | | B | C | B | B |

The results are listed in Table 2. Further, the obtained HPLC spectrum is shown in FIG. 2(b).

Comparative Example 2

The procedures were the same as those in Example 4 except that pure water was not added. The results are listed in Table 2. Further, the obtained HPLC spectrum is shown in FIG. 2(c).

Example 6

Figure 3A:
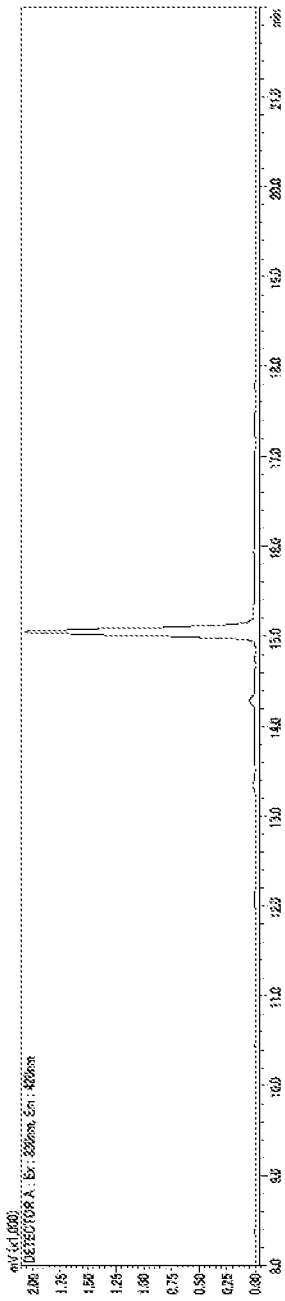
FIGS. 3(a) to 3(c) show HPLC spectra obtained in Examples 6 and 7 and Comparative Example 3.

The procedures were the same as those in Example 1 except that the amount of maltoheptaose was changed to 3 μg and the amount of pure water was changed to 4 μL. The results are listed in Table 2. Further, the obtained HPLC spectrum is shown in FIG. 3(a).

Example 7

Figure 3B:
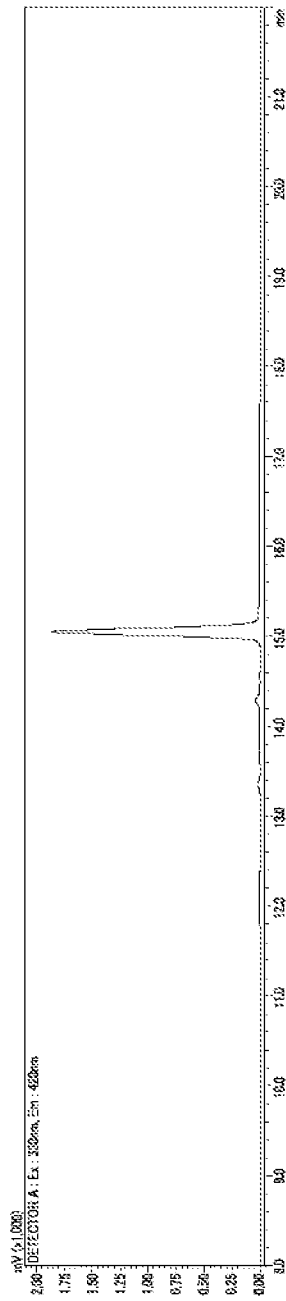

The procedures were the same as those in Example 6 except that the amount of pure water was changed to 8 μL. The results are listed in Table 2. Further, the obtained HPLC spectrum is shown in FIG. 3(b).

Comparative Example 3

Figure 3C:
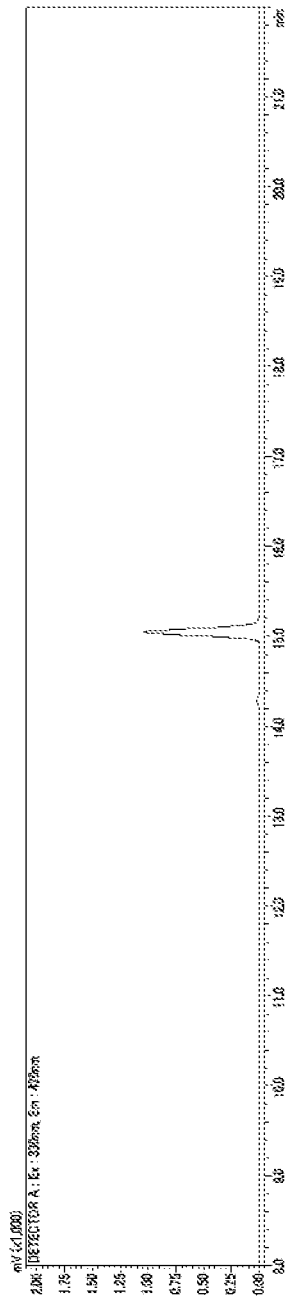

The procedures were the same as those in Example 6 except that pure water was not added. The results are listed in Table 2. Further, the obtained HPLC spectrum is shown in FIG. 3(c).

Example 8

Figure 4A:
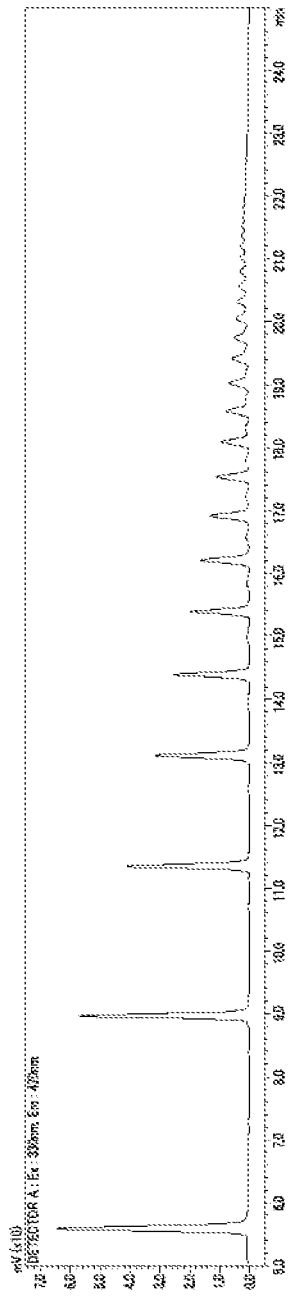
FIGS. 4(a) to 4(c) show HPLC spectra obtained in Examples 8 and 9 and Comparative Example 4.

The procedures were the same as those in Example 4 except that the maltoheptaose was changed to a glucose oligomer (a sugar chain: mixture of a plurality of kinds of oligosaccharides having different lengths of oligomers) dried with a centrifugal evaporator. The results are listed in Table 3. Further, the obtained HPLC spectrum is shown in FIG. 4(a).

Example 9

Figure 4B:
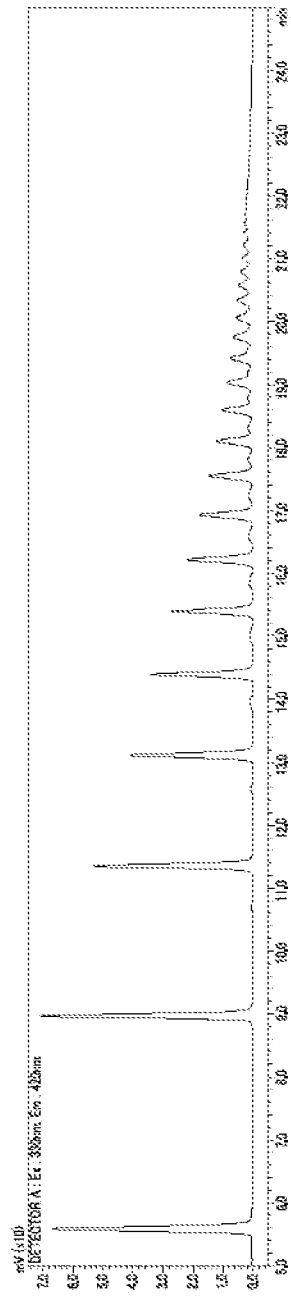

The procedures were the same as those in Example 8 except that the amount of pure water was changed to 8 μL. The results are listed in Table 3. Further, the obtained HPLC spectrum is shown in FIG. 4(b).

Comparative Example 4

Figure 4C:
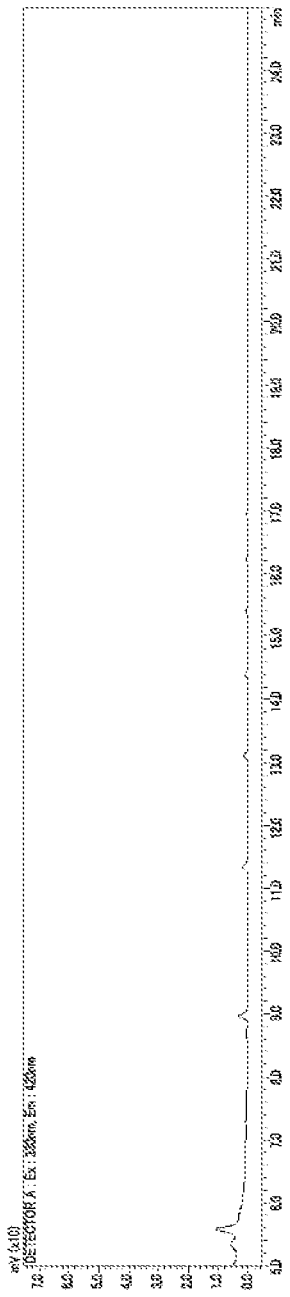

The procedures were the same as those in Example 8 except that pure water was not added. The results are listed in Table 3. Further, the obtained HPLC spectrum is shown in FIG. 4(c).

TABLE 3

|  | Unit | Comparative Example 4 | Example 8 | Example 9 |
| --- | --- | --- | --- | --- |
| Water amount X | μL | 0 | 4 | 8 |
| Sugar chain amount Y | μg | 1 | 1 | 1 |
| X/Y |  | 0 | 4.0 | 8.0 |
| Peak area value |  | 95287 | 1680062 | 2104567 |
| Peak area ratio |  | 1 | 17.63 | 22.09 |
| Labeling efficiency |  | — | A | A |

Experiment Example 1

The procedures were the same as those in Example 1 except that the amount of maltoheptaose was changed to 1 μg and the amount of pure water was changed to 1 μL. The results are listed in Table 4.

Experiment Example 2

The procedures were the same as those in Example 1 except that the amount of pure water was changed to 50 μL. The results are listed in Table 4.

Experiment Example 3

The procedures were the same as those in Example 1 except that the amount of pure water was changed to 100 μL. The results are listed in Table 4.

Further, Experiment Example 1 corresponds to Comparative Example 5, Experiment Example 2 corresponds to Example 10, and Experiment Example 3 corresponds to Comparative Example 6.

TABLE 4

|  | Unit | Experiment Example 1 | Experiment Example 2 | Experiment Example 3 |
| --- | --- | --- | --- | --- |
| Water amount X | μL | 1 | 50 | 100 |
| Sugar chain amount Y | μg | 1 | 1 | 1 |
| X/Y |  | 1.0 | 50 | 100 |
| Peak area value |  | 401068 | 3483113 | 2003562 |
| Peak area ratio |  | 0.27 | 2.31 | 1.33 |
| Labeling efficiency |  | C | A | B |
| Peak area ratio per sugar chain amount |  | 0.18 | 1.54 | 0.89 |
| Labeling properties |  | C | B | C |

(Evaluation of Labeling Efficiency)

A peak area value S1 was calculated from the obtained HPLC spectra of each example and each experiment example and a peak area value S0 was calculated from the obtained HPLC spectra of each comparative example. In a case where a plurality of peaks were present in the HPLC spectra, the sum (total value) of the peak areas of each peak was set as a peak area value.

Further, in a case where Examples 1 to 3 were carried out based on Comparative Example 1, Examples 4 and 5 and Experiment Examples 1 to 3 were carried out based on Comparative Example 2, Examples 6 and 7 were carried out based on Comparative Example 3, and Examples 8 and 9 were carried out based on Comparative Example 4 (in a case where the sugar chain amount and the water amount were measured under the same conditions as those in the examples and the comparative example in which the reaction environment of the sugar chain and the labeling reagent did not contain water was used as a reference), the ratio of the peak area value S1 of each example or each experiment example to the peak area value S0 of the comparative example used as a reference was set as a peat area ratio (S1/S0).

The peak area ratios in the HPLC spectra in each example and each experiment example were evaluated based on the following evaluation standard. The evaluation results are listed in Tables 2, 3, and 4. In Tables 2, 3, and 4, "-" indicates the comparative example used as a reference. The peak area ratio (S0/S0) of the comparative example used as a reference was set to 1.

A: The peak area ratio was greater than or equal to 1.5.
B: The peak area ratio was greater than or equal to 1.0 and less than 1.5.
C: The peak area ratio was less than 1.0.

(Evaluation of Labeling Properties)

In a case where the peak area ratio (S0/Y of Comparative Example 1) per the sugar chain amount of Comparative Example 1 was used as a reference, the ratio (the ratio of the peak area value per the sugar chain amount) of the peak area value (S0/Y or S1/Y) in the HPLC spectrum per the sugar chain amount Y (μg) to S0/Y of Comparative Example 1 used as a reference was calculated in each example, each comparative example, and each experiment example.

The peak area ratios per the sugar chain amount in each example, each comparative example, and each experiment example were evaluated based on the following evaluation standard. The evaluation results are listed in Tables 2 and 4. In Tables 2 and 4, "-" indicates Comparative Example 1 used as a reference. The peak area ratio (S0/Y of Comparative Example 1) per the sugar chain amount of Comparative Example 1 used as a reference was set to 1 (reference value).

B: The peak area value ratio per the sugar chain amount was greater than 1 used as a reference value.

C: The peak area value ratio per the sugar chain amount was less than or equal to 1 used as a reference value.

It was understood that the labeling efficiency and the labeling properties of the labeling method of Examples 1 to 7 were improved compared to each comparative example used as a reference. It was understood that the labeling efficiency of the labeling method of Examples 8 and 9 was improved compared to Comparative Example 4 used as a reference.

Further, in the sugar chain labeling method of Experiment Example 1 (Comparative Example 5), an effect in which the labeling efficiency and the labeling properties were decreased compared to Comparative Example 2 used as a reference was obtained. In the sugar chain labeling method of Experiment Example 2 (Example 10), an effect in which the labeling efficiency and the labeling properties were improved compared to Comparative Example 2 used as a reference was obtained. In the sugar chain labeling method of Experiment Example 3 (Comparative Example 6), an effect in which the labeling efficiency was slightly improved, but the labeling properties were decreased compared to Comparative Example 2 used as a reference was obtained.

Hereinbefore, the present invention has been described in detail based on the embodiments and the examples, but these are merely examples and other various configurations can be employed.

This application claims priority based on Japanese Patent Application No. 2017-074655, filed on Apr. 4, 2017, the contents of which are incorporated herein by reference.

The invention claimed is:

1. A method for preparing a sugar chain, comprising:
adjusting a volume of water added to a sugar chain-containing sample so as to obtain a labeling sample where a ratio (X/Y) of the volume of the water (X, in μL) to an amount of the sugar chain (Y, in μg) is greater than or equal to 1.2 and less than or equal to 50, and
adding a labeling reagent to the labeling sample to obtain a labeled product containing a labeled substance of the sugar chain,
wherein the method further comprises before adding the water to the sugar chain-containing sample, heating the sugar chain-containing sample to remove at least some of a solvent contained in the sugar chain-containing sample.

2. The method for preparing a sugar chain according to claim 1,
wherein a reaction between the labeling reagent and the sugar chain is carried out in a container.

3. The method for preparing a sugar chain according to claim 2,
wherein the container has a tube shape.

4. The method for preparing a sugar chain according to claim 1, further comprising:
before adding the water to the sugar chain-containing sample, an isolation step of acting a sugar chain-isolating enzyme on a sample in a state of being fixed to a solid phase to obtain the sugar chain-containing sample.

5. The method for preparing a sugar chain according to claim 4,
wherein the sugar chain-isolating enzyme contains peptide N-glycanase or endo-β-N-acetylglycosaminidase.

6. The method for preparing a sugar chain according to claim 4,
wherein the solid phase has a column or a cartridge structure.

7. The method for preparing a sugar chain according to claim 4, further comprising:
a separation step of performing solid-liquid separation after the isolation step to obtain a separate liquid which contains the sugar chain.

8. The method for preparing a sugar chain according to claim 1,
wherein the labeling reagent contains a compound which contains an amino group having UV absorption characteristics or fluorescence characteristics, a reducing agent, and an organic solvent.

9. The method for preparing a sugar chain according to claim 8,
wherein the compound which contains an amino group contains 2-aminobenzamide.

10. The method for preparing a sugar chain according to claim 8,
wherein the reducing agent contains one or more selected from the group consisting of sodium cyanoborohydride, sodium triacetoxyborohydride, methylamine borane, dimethylamine borane, trimethylamine borane, picoline borane, and pyridine borane.

11. The method for preparing a sugar chain according to claim 8,
wherein the organic solvent contains one or more selected from the group consisting of an aprotic polar organic solvent, a protic polar organic solvent, and an aprotic non-polar organic solvent.

12. The method for preparing a sugar chain according to claim 1, wherein the sugar chain is derived from a glycoprotein.

* * * * *